(12) United States Patent
Bert et al.

(10) Patent No.: US 8,598,546 B2
(45) Date of Patent: Dec. 3, 2013

(54) METHOD AND APPARATUS FOR IRRADIATION OF A TARGET VOLUME

(75) Inventors: Christoph Bert, Aschaffenburg (DE); Eike Rietzel, Weiterstadt (DE); Martin Rohregger, Munich (DE)

(73) Assignees: GSI Helmholtzzentrum fur Schwerionenforschung GmbH, Darmstadt (DE); Siemens Aktiengesellschaft, Munich (DE)

( * ) Notice: Subject to any disclaimer, the term of this patent is extended or adjusted under 35 U.S.C. 154(b) by 161 days.

(21) Appl. No.: 12/918,421

(22) PCT Filed: Feb. 16, 2009

(86) PCT No.: PCT/EP2009/001058
§ 371 (c)(1),
(2), (4) Date: Aug. 19, 2010

(87) PCT Pub. No.: WO2009/103467
PCT Pub. Date: Aug. 27, 2009

(65) Prior Publication Data
US 2010/0327188 A1  Dec. 30, 2010

(30) Foreign Application Priority Data
Feb. 19, 2008 (DE) .......................... 10 2008 009 765

(51) Int. Cl.
*A61N 5/00* (2006.01)
(52) U.S. Cl.
USPC ..................................... 250/492.3; 250/492.1
(58) Field of Classification Search
USPC ................. 250/492.1, 492.2, 492.22, 492.3
See application file for complete search history.

(56) References Cited

U.S. PATENT DOCUMENTS

| 7,102,144 | B2 | 9/2006 | Matsuda et al. |
| 2006/0259282 | A1 | 11/2006 | Failla et al. |
| 2007/0034812 | A1 | 2/2007 | Ma et al. |
| 2007/0228305 | A1 | 10/2007 | Keppel et al. |

(Continued)

FOREIGN PATENT DOCUMENTS

| DE | 102005063220 A1 | 6/2007 |
| WO | WO 2007079854 A2 | 7/2007 |
| WO | WO 2008116535 A1 | 10/2008 |

OTHER PUBLICATIONS

Bert et al., 4D treatment planning for scanned ion beams, Radiation Oncology, 20070703 BioMed Central Ltd, Lo—ISSN 1748-717X, vol. 2, Nr: 1, p. 24, XP021030775.

(Continued)

*Primary Examiner* — Robert Kim
*Assistant Examiner* — Hanway Chang
(74) *Attorney, Agent, or Firm* — Leydig, Voit & Mayer, Ltd.

(57) ABSTRACT

A method of generating a data set defining a plurality of target points in a target volume in a body at which a particle beam is to be directed in a continuous or discontinuous process includes directing a particle beam to each of the target points so as to provide a spatial dose distribution in an area around the respective target point. The target points include a first target point having z-spacing, measured in a direction of the particle beam in a homogenous body equivalent to the body, from an adjacent second target point at a higher or lower particle energy. The method also includes defining the target points in the data set by at least one of the z-spacing and the spatial dose distribution in dependence upon a particle energy of the respective target point.

28 Claims, 8 Drawing Sheets

(56) References Cited

U.S. PATENT DOCUMENTS

2007/0295910 A1   12/2007   Harada
2009/0095921 A1   4/2009    Bert et al.
2010/0108903 A1   5/2010    Bert et al.

OTHER PUBLICATIONS

Bert, Bestrahlugsplanung für bewegte Zielvolumina in der Tumortherapie mit gescanntern Kohlenstoffstrahl, XP002481370.
International Search Report for PCT/EP2009/001058 mailed on Apr. 22, 2009.

METHOD AND APPARATUS FOR IRRADIATION OF A TARGET VOLUME

CROSS REFERENCE TO PRIOR APPLICATIONS

This application is a U.S. National Phase application under 35 U.S.C. §371 of International Application No. PCT/EP2009/001058, filed on Feb. 16, 2009, which claims benefit to German Application No. DE 10 2008 009 765.6, filed Feb. 19, 2008. The International Application was published in English on Aug. 27, 2009 as WO 2009/103467 under PCT Article 21 (2).

FIELD

The present disclosure relates to a method and an apparatus for determination of control parameters of an irradiation system for irradiation of a predetermined target volume in a raster scanning method or in a spot scanning method or in a continuous scanning method or in some other scanning method.

BACKGROUND

Tumour therapy using particle beams, especially using protons, a particles and carbon nuclei, is increasing in importance. In that context, the raster scanning method has a number of advantages over other methods. In this method, a three-dimensional raster is placed over the tumour volume. The particle beam is deflected by deflecting magnets in two directions perpendicular to one another (the x and the y directions). By actively varying the particle energy, the position of the Bragg peak, in which the largest portion of the dose is deposited, is set at differing depths (z direction) in the body.

The dose which is to be administered as a function of the location is specified or prescribed by a user after thorough diagnosis. For example, the dose within the tumour should be as constant as possible and should fall off as steeply as possible outside the tumour. A more complex dependency of the dose on the location is also possible, however. As accurate as possible adherence to the dose is an important prerequisite for successful treatment.

Discrepancies between the dose actually administered and the dose prescribed, which is referred to hereinbelow also as the desired dose, can come about as a result of a variety of causes. Such causes include inter alia discrepancy between the location of the particle beam and the intended location and also movements of the patient or parts of the patient during the irradiation.

In order to reduce the effects of such influences, there are chosen inter alia as fine as possible a raster of target points of the particle beam and as large as possible an extent of the particle beam. The finer the raster, however, the longer the duration of irradiation, because every change in the deflection of the particle beam in the x or y direction and every change in the particle energy requires a certain amount of time. In particular, a change in the particle energy requires numerous changes and adjustments to the settings of magnets of the accelerator and the beam transport unit. Those changes and adjustments require a period of time which has a significant effect on the total duration of the irradiation. The larger the spatial region over which the dose administered or produced by direction of the particle beam at a selected target point, the more shallowly the dose falls off at the edge of the target volume. The larger the cross-section of a particle beam, the lesser is also the accuracy with which its position can be monitored, for example by means of a multi-wire proportional counter. Accordingly, a compromise is necessary in respect of spacings between isoenergy layers and the breadth of the dose distribution resulting from the direction of the particle beam at a single target point.

Similar problems exist not only in the case of irradiation of a tumour in a patient, but also in the case of many other applications in which a target volume in any (animate or inanimate) body is irradiated with a particle beam. Examples that may be mentioned are the irradiation of anatomical models in the context of research work or in the context of the quality checking or quality assurance of a system and the irradiation of materials in materials research or for modifying the properties thereof.

SUMMARY

In an embodiment, the present invention provides a method of generating a data set defining a plurality of target points in a target volume in a body at which a particle beam is to be directed in a continuous or discontinuous process. The method includes directing a particle beam to each of the target points so as to provide a spatial dose distribution in an area around the respective target points. The target points include a first target point having z-spacing, measured in a direction of the particle beam in a homogenous body equivalent to the body, from an adjacent second target point at a higher or lower particle energy. The method also defines the target points in the data set by at least one of the z-spacing and the spatial dose distribution in dependence upon a particle energy of the respective target point.

BRIEF DESCRIPTION OF THE DRAWINGS

Exemplary embodiments are described in detail below with reference to the accompanying Figures.

DETAILED DESCRIPTION

The disclosure provides an improved method of generating a data set and an improved controller for controlling a system for irradiation of a target volume using a scanning method.

The improvement is provided by a method, a computer program product, a controller and a system as described herein.

The present disclosure is based on the concept of varying the spacings between next adjacent target points measured in the direction of the particle beam or of varying the spatial distribution of the dose, especially the spatial extent of the dose distribution, produced by directing the particle beam at a target point, within the target volume in dependence upon the particle energy.

A body to be irradiated can have a spatially varying density, a spatially varying nuclide composition and other spatially varying properties which influence the interaction of the particle beam with the matter of the body. In bone, connective tissue, muscle tissue, fat, air or water, for example, protons, helium ions, oxygen ions, carbon ions or neon ions each have different ranges, produce different spectra of secondary radiation and, with the same particle energy and the same particle fluence, each produce different doses. Spacings measured in the direction parallel to the particle beam are therefore to be understood here and hereinbelow as being corresponding spacings in a homogeneous body which is equivalent to the inhomogeneous body actually being irradiated in terms of its interaction with the particle beam. Alternatively, however, the spacings in the body actually being irradiated can also be used.

A target point here and hereinbelow is a location definable, for example, by giving three Cartesian spatial co-ordinates (x, y, z), which location is generally located within the body being irradiated and especially within the target volume where a non-vanishing dose is to be administered. A particle beam here and hereinbelow is a beam of defined cross-section consisting of the ions already mentioned above by way of example or of other particles having a defined, generally narrow spectrum of the particle energy. The particle energy here and hereinbelow is the energy of the individual particle on entry into the body being irradiated.

Here and hereinbelow, whenever reference is made to a particle beam which is directed at a target point, it means that the particle beam is so guided (for example by deflecting magnets) in the x and y directions that the target point is located, for example, in the focal point or on a line (or on the extension thereof) of maximum fluence or dose, and that the target point is located in the Bragg peak of the particle beam.

In the direction parallel to the particle beam, the spatial distribution of the dose which, when directing the particle beam at a target point, is produced in the area around that target point, can be controlled by means of the spectrum of the particle energy. A sharply defined energy of the particle beam results in a sharply defined Bragg peak. The broader the energy spectrum of the particle beam, the wider is the Bragg peak. From an originally monoenergetic particle beam it is possible to produce, for example by means of a ripple filter, a particle beam having a broad energy spectrum.

In the x and y directions the spatial distribution of the dose produced in the area around a target point by a particle beam directed at that target point is determined by the cross-section of the particle beam.

It is possible for the spacing between next adjacent target points, measured in the direction parallel to the particle beam, and/or for the spatial dose distribution produced in the area around a target point by directing the particle beam at that target point to be dependent upon the energy of the particles entering the body being irradiated, for example, when the target points are arranged in isoenergy layers. All target points within an isoenergy layer are associated with the same particle energy. Within a homogeneous body which the particle beam enters through a boundary surface perpendicular thereto, isoenergy layers are planar. In an inhomogeneous body or in a body which the particle beam enters through a boundary surface of any shape, an isoenergy layer generally has a complex spatial form. When the target points are arranged in isoenergy layers, the spacing, measured in the direction parallel to the particle beam, of target points next adjacent in that direction is the spacing of the isoenergy layers measured in the same direction.

The spacing, measured in the direction parallel to the particle beam, between target points next adjacent in that direction or the spatial dose distribution can, however, be varied in dependence upon the particle energy in the case of any arrangement of the target points. The particle beam can be directed at the target points within the target volume in succession in a continuous or quasi-continuous process or in a discontinuous process, for example in the context of a raster scanning method, a spot scanning method, a continuous scanning method or some other scanning method.

The spacing, measured in the direction parallel to the particle beam, of target points next adjacent in that direction and/or the spatial dose distribution produced on direction of the particle beam at a target point can be a monotonic function or a strictly monotonic function of the particle energy within the entire target volume or within sub-regions of the target volume.

For some applications it can be especially advantageous to select spacings, measured in the direction parallel to the particle beam, of target points next adjacent in that direction to be larger at a lower particle energy than at a higher particle energy. Target points at a lower particle energy have generally already received a pre-dose during the irradiation of target points located behind them at a higher particle energy. At least if inhomogeneities of the irradiated body are not too abrupt in the direction parallel to the particle beam, that pre-dose is generally only slightly location-dependent. While adhering to constant requirements in terms of the accuracy with which the total dose administered should correspond to the prescribed dose, it is possible, as a result of the increasing pre-dose at decreasing particle energies, for the spacing, measured in the direction parallel to the particle beam, of target points next adjacent in that direction to be increasingly large at decreasing particle energies. The reduction in the number of target points so achieved results, at the same time, in a speeding-up of the irradiation operation with associated positive effects for the patient and for the irradiation system. To improve homogeneity and to reduce the unevenness of the total dose, as the particle energy decreases it is possible at the same time for the width of the Bragg peak to be increased.

On the basis of such deliberations, as the particle energy decreases it is possible to select a decreasing cross-section of the particle beam and/or a decreasing width of the Bragg peak. The resultant tendency towards an increase in the unevenness or inhomogeneity of the administered dose is compensated by the relatively high homogeneity of the pre-dose which increases as particle energy decreases.

In addition to the spacing, measured in the direction parallel to the particle beam, of target points next adjacent in that direction and/or in addition to the spatial distribution of the dose produced in the area around an individual target point by directing the particle beam at that target point, it is also possible for the spacing, measured in the direction perpendicular to the particle beam, of target points next adjacent in that direction to be varied as a function of the particle energy. For example, the influence of a decreasing cross-section of the particle beam on the homogeneity of the dose administered or on the accuracy with which the dose administered corresponds to the dose prescribed can be partially or fully compensated by a simultaneously decreasing spacing, measured in the direction perpendicular to the particle beam, of target points next adjacent in that direction.

When the target points are arranged in isoenergy layers, for many applications it can be advantageous for the spacing between next adjacent isoenergy layers to be reduced, especially to a minimum distance, at least when an isoenergy layer protrudes over isoenergy layers at higher particle energies in a direction perpendicular to the particle beam and thus has target points without a pre-dose.

Further optimisation is possible when the spacing of two next adjacent isoenergy layers is specified in dependence upon the dose to be produced by directing the particle beam at target points in one of the two isoenergy layers or upon the difference between the desired dose and the pre-dose. For that purpose, first pre-doses are calculated for some or all target points in a selected isoenergy layer, the pre-doses being produced at target points in the selected isoenergy layer by directing the particle beam at target points in isoenergy layers with a higher particle energy. The spacing of the next isoenergy layer with the next lowest particle energy can then be specified in dependence upon the pre-doses, especially the minimum of the calculated pre-doses, and the desired doses. Alternatively, after the calculation of the pre-doses and in dependence upon the calculated pre-doses and the desired doses, the spacing of the selected isoenergy layer from the next adjacent isoenergy layer with a higher particle energy is adjusted or optimised. That optimisation can take place iteratively. Corresponding specifying or optimisation of the spacings measured in the direction parallel to the particle beam is also advantageous when the target points are not arranged in isoenergy layers. The width of the Bragg peak can also be specified or optimised in a corresponding way in dependence upon calculated pre-doses and prescribed desired doses.

Each of the described methods can, in addition, be configured such that the z spacings and/or spatial dose distributions at the individual target points, selected in dependence upon the particle energy respectively, are, in addition, selected in dependence upon a movement of the target volume being irradiated or of a portion of the target volume. The movement of the target volume being irradiated can be an actual movement measured during the irradiation or a movement to be expected during the irradiation. The movement expected during the irradiation is based, for example, on empirical data.

The movement taken into consideration in the selection or setting of z spacings and/or spatial dose distributions can be a natural movement, for example caused by breathing, heartbeat, peristalsis or movements of the digestive organs. For example, when a lung is being irradiated, a typical movement of the lung can be assumed, whereas when a prostate is being irradiated, a different, typical movement that customarily occurs in irradiation of the prostate can be assumed. Alternatively, the movement taken into consideration can be a residual movement that remains when a technique for reducing the effects of movement is employed. Techniques for reducing the effects of movement are known, for example, as gating or tracking.

In the described particle-energy-dependent specifying of spacings or spatial dose distributions it is therefore possible also to take into consideration whether, in which direction and to what extent a target point can be periodically or aperiodically moved or displaced from its normal position by breathing, heartbeat or some other cause during irradiation.

Many aspects of the present disclosure can be realised both in a method of generating a data set which defines a multiplicity of target points in a target volume in a body being irradiated and in a method of controlling an irradiation system, in a computer program product, an irradiation system or a controller for controlling such a system.

Figure 1:
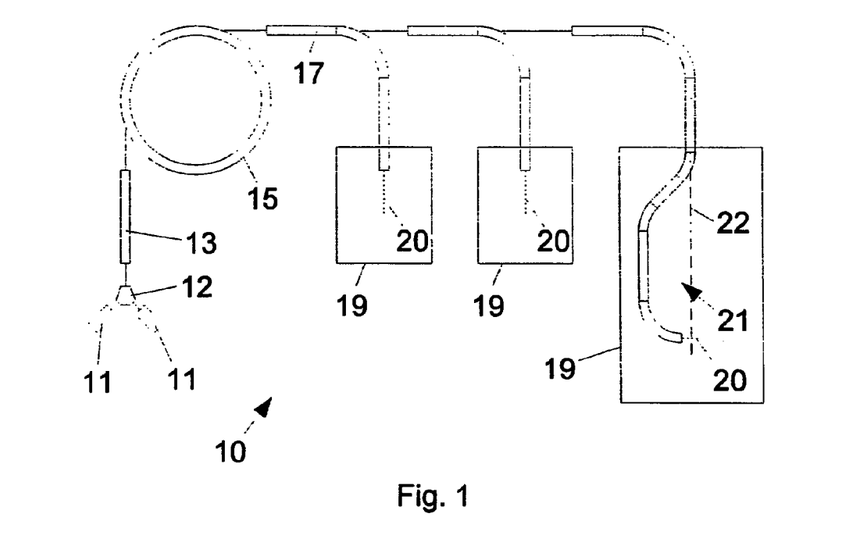
FIG. 1 shows, in diagrammatic form, an irradiation system.

FIG. 1 shows, in diagrammatic form, an overview of the structure of an irradiation system 10 as an example of any system for irradiating a body, especially tissue in the body affected by tumour disease, with a particle beam. The system may also be used to irradiate inanimate material, like phantoms, etc. . . . The particles used are mainly ions, for example protons, pions, helium ions, carbon ions, neon ions etc.

Usually, such particles are produced in a particle source 11. If, as shown in FIG. 1, there are two particle sources 11, which produce two different ion types, it is possible to switch over between those two ion types within a short time interval. For this purpose there is used, for example, a switching magnet 12 which is arranged between the ion sources 11 on the one hand and a pre-accelerator 13 on the other hand.

Examples that may be mentioned of two different ion types which can be used alternatively in an irradiation system are helium ions ($^3$He or $^4$He) and carbon ions. These differ in the biological effect of their beams and are especially suitable for different types of tumours. $^4$He and $^{12}$C both have, in the fully ionised state, the same A/Q ratio between the mass number A and charge Q. They can therefore be accelerated in the same accelerator system without major adaptation.

The ions produced by the ion source 11 or by one of the ion sources 11 and, where applicable, selected using the switching magnet 12 are accelerated to a first energy level in the pre-accelerator 13. The pre-accelerator 13 is, for example, a linear accelerator (LINAC for: "LINear ACcelerator"). The ions are then fed into an accelerator 15, for example a synchrotron or cyclotron. In the accelerator 15 they are accelerated to high energies such as are required for the purpose of irradiation. After the ions leave the accelerator 15, a high-energy beam transport system 17 guides the particle beam to one or more irradiation rooms 19. In an irradiation room 19, the accelerated particles are directed at a body to be irradiated. Depending on the particular arrangement, this is carried out from a fixed direction (in so-called "fixed beam" rooms") or, however, from different directions by means of a rotatable gantry 21 which can be moved about an axis 22.

Figure 2:
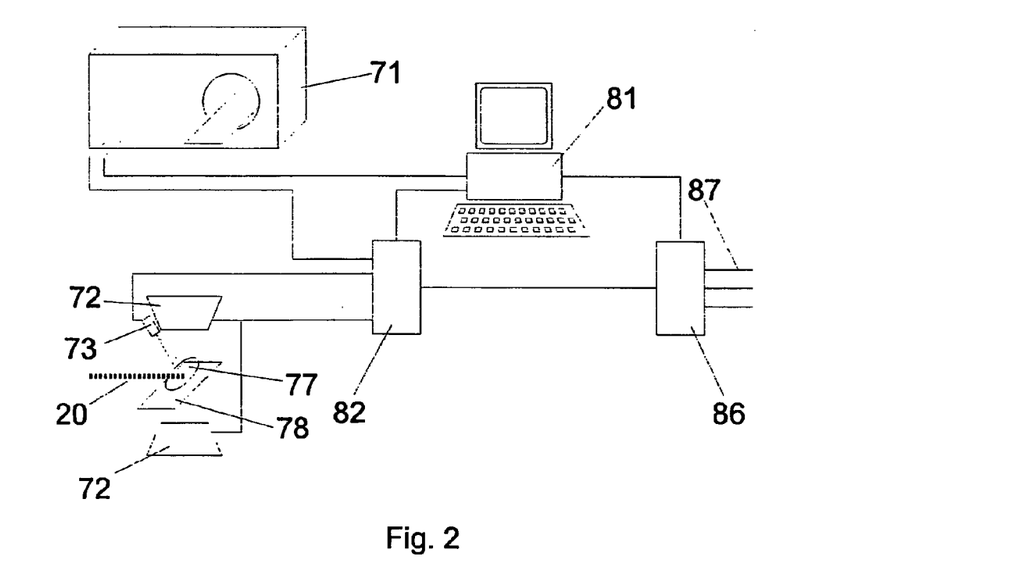
FIG. 2 shows, in diagrammatic form, devices suitable for use for irradiation planning, for generating a data set or for controlling an irradiation operation.

FIG. 2 shows, in diagrammatic form, devices which can be used in irradiation planning, for generating a data set that defines target points in a target volume in a body, and for controlling an irradiation system, for example as described above with reference to FIG. 1.

By means of a computer tomograph or nuclear spin tomograph 71 or by means of some other diagnostic device it is possible to determine the position and extent of a tumour to be irradiated or of some other target volume. Data from the tomograph 71 are processed immediately or after a preparation step by means of further devices (not shown in FIG. 2) in an apparatus 81 for creating a data set. The apparatus 81 is, for example, a desktop computer, a workstation or some other computer. Optionally, the apparatus 81, by virtue of its user interface, software or other features, is also suitable for enabling medical personnel to define therein the target volume, the doses to be administered, the division thereof into a number of fractions, the direction of irradiation and other details of the particle therapy.

The body 77 being irradiated can be monitored using variously constructed monitoring devices before, during or after the irradiation by means of the system 10. For example, a PET camera 72 (PET=Positron Emission Tomography) and/or a distance sensor 73 are provided for detecting a body 77 to be irradiated which is resting on a support surface 78. The PET camera 72 and/or the distance sensor 73 and the support surface 78 can be arranged inside one of the irradiation rooms 19 described above with reference to FIG. 1. In that case, by means of the PET camera 72 and/or the distance sensor 73 it is possible to detect the dose produced by a particle beam 20 as well as movements of the body 77 being irradiated. Alternatively, the PET camera 72, the distance sensor 73 and the support surface 78 are arranged outside an irradiation room. Alternatively or additionally, the body 77 can be monitored by means of a fluoroscopy device, an X-ray device, an ultrasonic sensor, a breathing belt and/or some other external sensor.

Data from the tomograph 71, from the PET camera 72 and from the distance sensor 73 can be processed by a device 82 for determining one or more movement parameters. By means of the device 82 it is possible for movements of sub-regions of the body 77 (for example caused by breathing or heartbeat) to be detected quantatively before irradiation or during irradiation. The movement parameter(s) determined by the device 82 can be taken into consideration by the apparatus 81 for creating a data set.

Data suitable for taking into consideration in the creation of a data set are especially data relating to the amplitudes of typical and/or periodic movements or relating to a correlation between the spatial position of the target volume and/or a variable detectable externally, for example by means of the distance sensor 73. Alternatively or additionally, data or parameters determined by the device 82 can be processed directly by a controller 86 for controlling an irradiation system 10, as described above with reference to FIG. 1. For that purpose there are suitable especially data detected by the PET camera 72 or the distance sensor 73 during irradiation. Also introduced into the controlling of the system 10 by the controller 86 is the data set created by the apparatus 81. The controller 86 is coupled to the irradiation system 10 by means of control lines 87 or in some other way.

The basic structure of an irradiation system 10 described with reference to FIG. 1 is typical of many particle therapy systems and other irradiation systems, but a different structure is also possible. The exemplary embodiments described hereinbelow are suitable for use both in connection with the irradiation system described with reference to FIG. 1 and the devices described above with reference to FIG. 2 as well as in connection with other irradiation systems and devices.

FIGS. 3 to 6 each show, in diagrammatic form, a sectional view of a target volume 40. The section planes shown are each defined by an x direction and a z direction, the x direction being arranged perpendicular to the direction of a particle beam irradiating the target volume 40 and the z direction being arranged parallel thereto. Both within and outside the target volume 40 there are shown target points 30 which are arranged in isoenergy layers 51 to 59. The particle beam is typically directed only at target points 30 located within the target volume 40.

When the target volume 40 is located in a body which is homogeneous in terms of its interaction with the particle beam being used and which the particle beam enters through an interface perpendicular to the particle beam, the isoenergy layers 51 to 59, as shown in FIGS. 3 to 6, are planar. Otherwise, the views in FIGS. 3 to 6 are to be understood as being views of corresponding sections through bodies that are homogeneous in terms of their interaction with the particle beam and are equivalent to the bodies actually to be irradiated (for example water equivalents) with a planar interface perpendicular to the particle beam.

Figure 3:
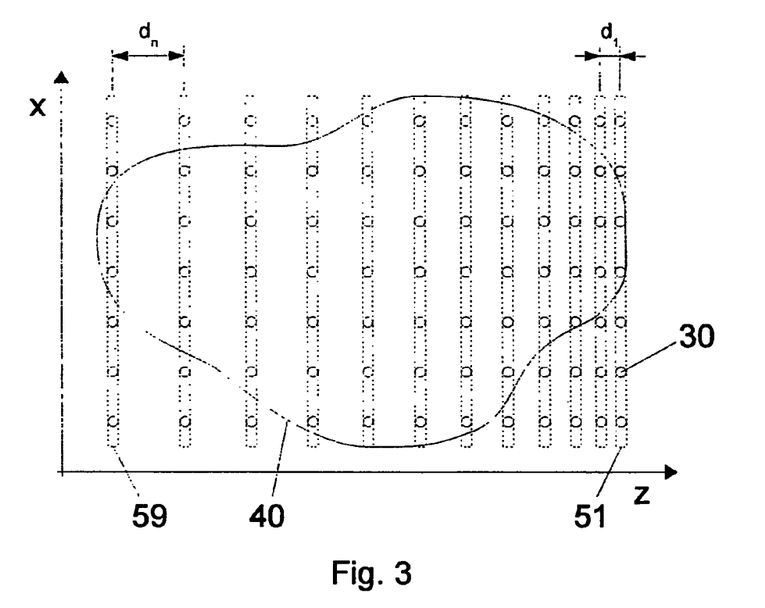
FIG. 3 shows, in diagrammatic form, target points in a plurality of isoenergy layers.
Figure 4:
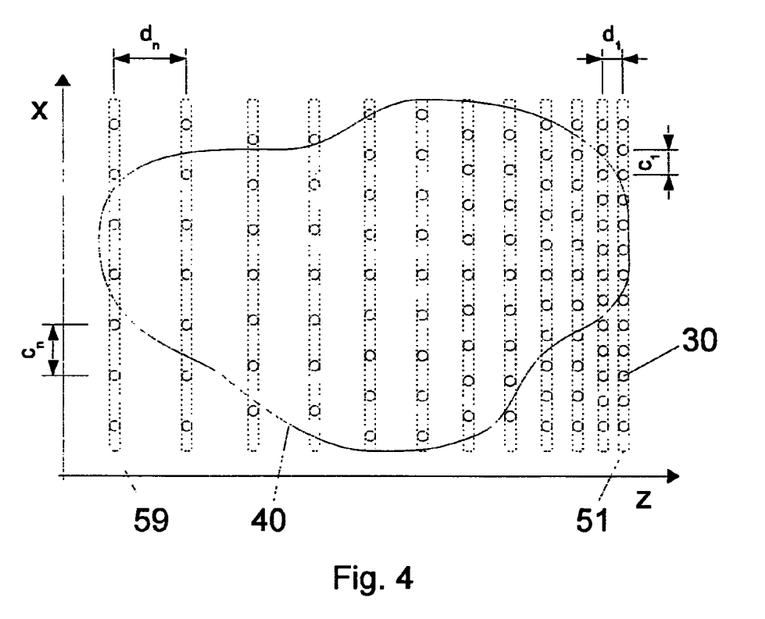
FIG. 4 shows, in diagrammatic form, target points in a plurality of isoenergy layers.
Figure 5:
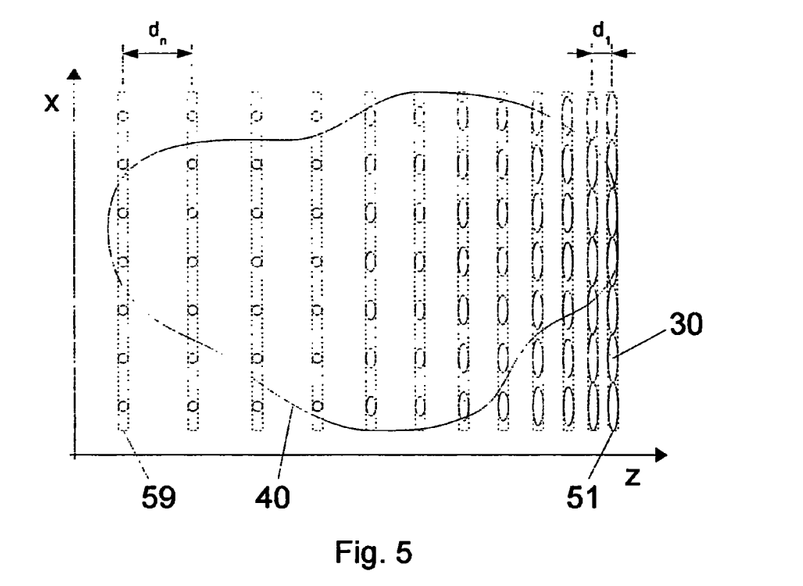
FIG. 5 shows, in diagrammatic form, target points in a plurality of isoenergy layers.
Figure 6:
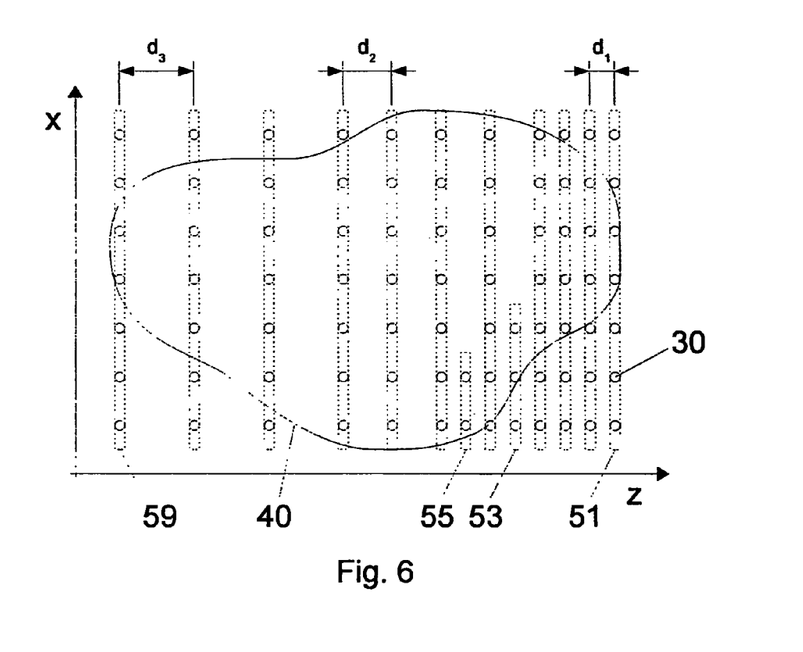
FIG. 6 shows, in diagrammatic form, target points in a plurality of isoenergy layers.

The number of target points 30 and the number of isoenergy layers 51 to 59 can each differ in any way from the views in FIGS. 3 to 6. In FIGS. 3, 4 and 6 the target points 30 are indicated by small circles. In FIG. 5 the target points 30 are in some cases also indicated by ellipses. The different extents of those ellipses in the x direction indicate that when the particle beam is directed at the target points 30 different spatial dose distributions are produced.

In each of the views of FIGS. 3 to 6, the particle beam is incident on the target volume 40 from the left and therefore in the positive z direction. The isoenergy layer 51 shown on the extreme right in each of FIGS. 3 to 8 is therefore referred to as the distal-most layer, while the isoenergy layer 59 shown on the extreme left is in each case referred to as the proximal-most isoenergy layer.

FIG. 3 shows an arrangement of the target points 30 in isoenergy layers 51 to 59, the spacings $d_1$ to $d_n$, of which increase from distal to proximal strictly monotonically. As a function of the particle energy, which, as mentioned, is always to be understood as the energy of the particles entering the body being irradiated, the spacing between next adjacent isoenergy layers falls strictly monotonically.

At a target point in a non-distal-most isoenergy layer, as a rule a dose is already produced or deposited when the particle beam is being directed at target points 30 in more distal isoenergy layers, which dose is herein termed a pre-dose. The more proximal the location of a target point, the higher as a rule is the pre-dose. Because distally of the Bragg peak only a very small and very rapidly falling dose is produced, the dose to be produced at a target point when a particle beam is directed thereat corresponds substantially to the difference between the prescribed dose, or desired dose, and the pre-dose.

The pre-dose, at least in the case of a homogeneous target volume 40, is only slightly location-dependent. In the case of a preset upper limit for the location dependency of the total dose, the higher the only slightly location-dependent pre-dose the greater can be the location dependency of the dose produced by direction of the particle beam at target points in an isoenergy layer under consideration. Because the pre-dose generally increases from distal to proximal, the spacing of next adjacent layers can therefore likewise increase. The resulting reduction in the total number of target points and especially the reduction in the number of isoenergy layers results in a speeding-up of the entire irradiation operation.

FIG. 4 shows a variant of the arrangement of the target points 30 in which, from distal to proximal, in addition to the spacing of next adjacent isoenergy layers also the spacing of next adjacent target points 30 within an isoenergy layer, measured in a direction perpendicular to the particle beam, increases from $c_1$ to $c_n$. Distally, in the case of small pre-doses, the desired accuracy of the administered dose, especially, for example, the desired low location-dependency of the administered dose, is achieved by small spacings between next adjacent isoenergy layers and by small spacings between the target points within an energy layer. Proximally, as a result of the high pre-dose, that requirement can be met by a larger spacing between next adjacent isoenergy layers and a larger spacing between target points within an isoenergy layer.

FIG. 5 shows a variant of the arrangement of target points described above with reference to FIG. 3 in which, similarly to FIGS. 3 and 4, distally there is used a small layer spacing which increases up to the proximal-most isoenergy layer 59. In addition, distally there is used a larger beam cross-section than proximally. The extent in the x direction of the ellipses used in FIG. 5 for indicating the target points 30 in each case indicates the different cross-sections of the particle beam. The varying cross-section of the particle beam produces a spatial dose distribution which, in the direction perpendicular to the particle beam, is greater distally than proximally.

In FIG. 6, most of the target points 30 are arranged in isoenergy layers 51 to 59 the spacings of which increase from the distal-most isoenergy layer 51 to the proximal-most isoenergy layer 59 in a number of stages. As a function of the particle energy, the spacings between next adjacent isoenergy layers decrease in stages. In the case of the distal-most isoenergy layer 51 and some adjacent isoenergy layers, the spacing between next adjacent isoenergy layers is $d_1$ in each case. In a proximal region adjoining the proximal-most isoenergy layer 59, the spacing between next adjacent isoenergy layers is $d_3$ in each case, where $d_3$ is greater than $d_1$. In a middle region, the spacing between next adjacent isoenergy layers is $d_2$, where $d_2$ is greater than $d_1$ and smaller than $d_3$.

It will be seen in FIGS. 3 to 6 that, as a result of the shape of the target volume 40, in the middle region there are also target points 30 which have only a very small pre-dose. In order that there too there is achieved a preset maximum difference between the dose actually administered and the desired dose, it is possible to introduce additional isoenergy layers. Such additional isoenergy layers are indicated by way of example in FIG. 6 by reference numerals 53 and 55, but can also be used in the arrangements of target points described with reference to FIGS. 3 to 5. Showing the additional isoenergy layers 53, 55 shortened in the x direction is intended to make it clear that in those additional isoenergy layers the particle beam is directed only at a small number of target points 30.

Figure 7:
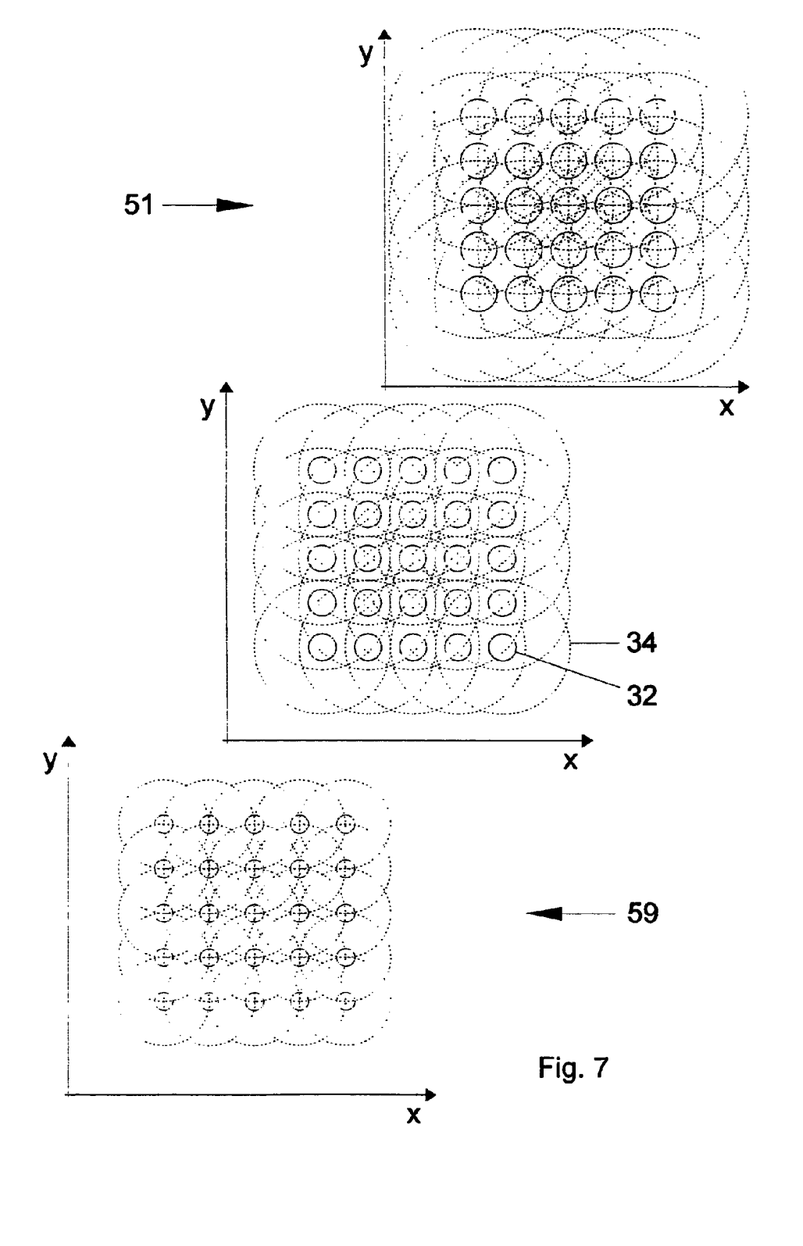
FIG. 7 shows, in diagrammatic form, dose distributions within an isoenergy layer.
Figure 8:
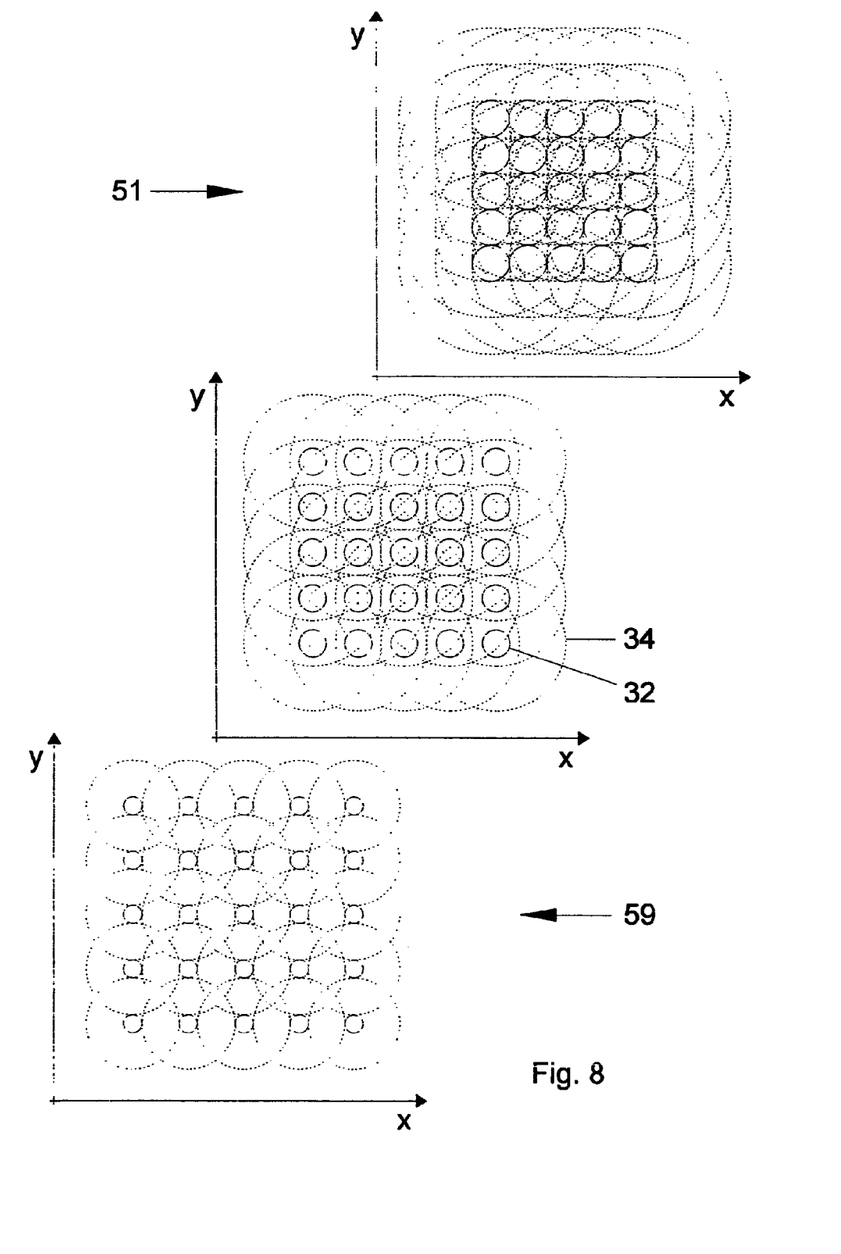
FIG. 8 shows, in diagrammatic form, dose distributions within an isoenergy layer.

FIGS. 7 and 8 each show, in diagrammatic form, dose distributions within an isoenergy layer that are generated by direction of the particle beam at the target points within the isoenergy layers shown. A distal isoenergy layer, especially the distal-most isoenergy layer 51 (see FIGS. 3 to 6), is in each case shown top right. A proximal isoenergy layer, especially the proximal-most isoenergy layer 59, is shown bottom left. In the middle each Figure shows an isoenergy layer in a middle region. The spatial dose distribution produced by direction of the particle beam at a target point is in each case shown in simplified form by two concentric circles 32, 34. Those two circles each represent amounts of locations of the same dose. For example, the dose to the smaller circle 32 is in each case 95% and to the larger circle 34 is in each case 30% of the maximum (central) dose. As a departure from the illustrations in FIGS. 7 and 8, the cross-section of a particle beam and the location-dependency of the dose thereby produced can differ from circular symmetry.

Both in FIG. 7 and in FIG. 8, the cross-section of the particle beam and the extent of the spatial distribution of the dose produced by direction of the particle beam at an individual target point decrease in both directions (x direction and y direction) perpendicular to the direction of the particle beam from the distal layer 51 to the proximal layer 59. While in FIG. 7 the spacings between the target points within the isoenergy layer remain constant from distal to proximal, in FIG. 8 those spacings increase.

Figure 9:
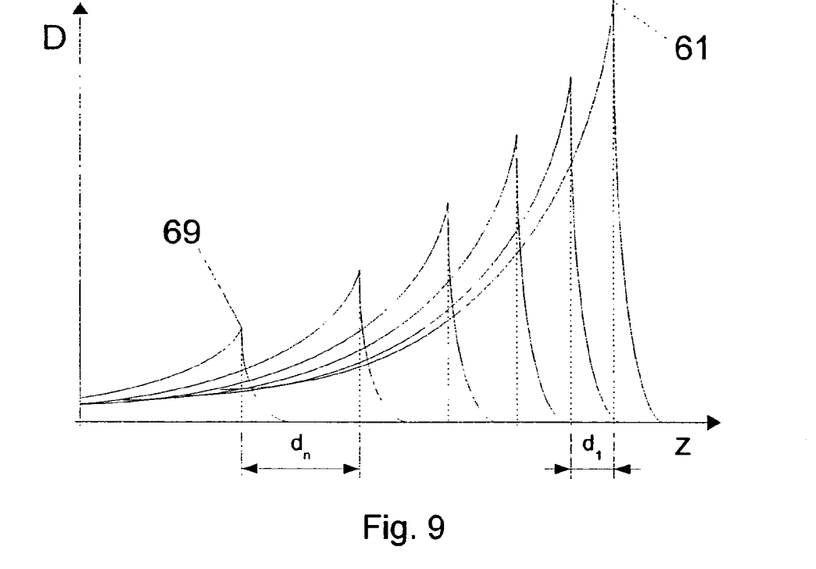
FIG. 9 shows, in diagrammatic form, Bragg peaks in a plurality of isoenergy layers.
Figure 10:
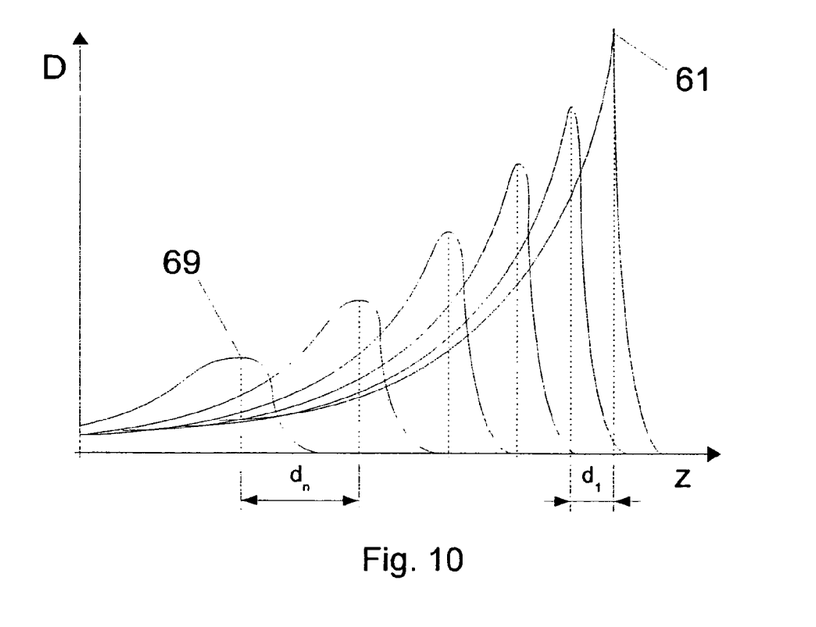
FIG. 10 shows, in diagrammatic form, Bragg peaks in a plurality of isoenergy layers.

FIGS. 9 and 10 show, in diagrammatic form, Bragg peaks 61 to 69 in a plurality of isoenergy layers, as shown, for example, in FIGS. 3 to 5. The abscissa is associated with the z-co-ordinates, the ordinate is associated with the dose D. In accordance with the pre-dose for each individual isoenergy layer, which pre-dose increases from distal to proximal, the dose maximum of the individual Bragg peak decreases from the distal-most Bragg peak 61 to the proximal-most Bragg peak 69. In FIGS. 9 and 10 it can also be seen that the spacings between the isoenergy layers or between the Bragg peaks 61 to 69 increase from distal to proximal from $d_1$ to $d_n$, similarly to the views in FIGS. 3 to 5.

The view in FIG. 10 differs from that in FIG. 9 in that, in addition, from distal to proximal an increasing breadth of the energy spectrum results in a corresponding increasing width of the Bragg peak. The increasing width of the Bragg peak partially or fully compensates for the influence of the increasing spacing between next adjacent isoenergy layers on the accuracy with which the dose actually administered corresponds to the desired dose. Variable broadening of the energy spectrum of the particle beam is possible, for example, by means of a variable ripple filter or by means of a plurality of ripple filters, which alternatively are brought into the beam path by means of a suitable device.

Alternatively, the width of the Bragg peak is selected to be greater for distal isoenergy layers than for proximal. The width of the Bragg peak can be a monotonic function or strictly monotonic function of the particle energy, for example a step function or a polynomial. In particular, for the width of the Bragg peak it is possible to select in almost all isoenergy layers a predetermined value and only for a small number of isoenergy layers at the distal margin a width that is enlarged in comparison therewith. A larger width of the Bragg peak for distal isoenergy layers in which there is only a very small pre-dose or no pre-dose resulting from the irradiation of isoenergy layers with an even higher particle energy enables the accuracy of the dose produced there to be increased.

Figure 11:
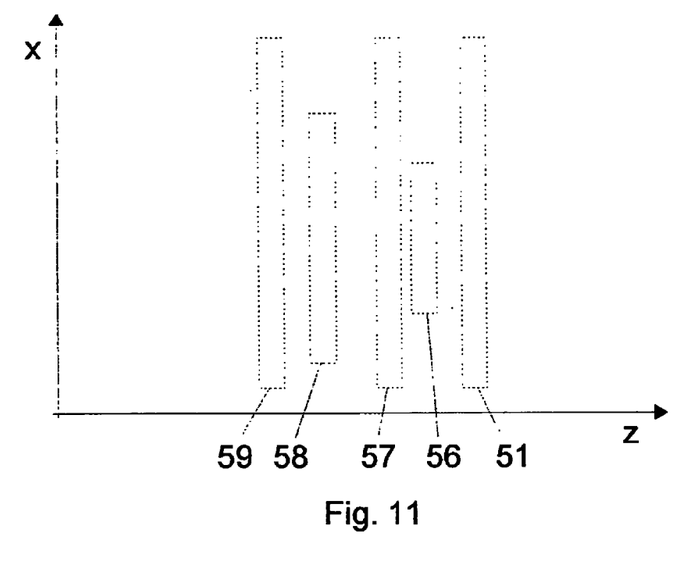
FIG. 11 shows, in diagrammatic form, a plurality of isoenergy layers.
Figure 12:
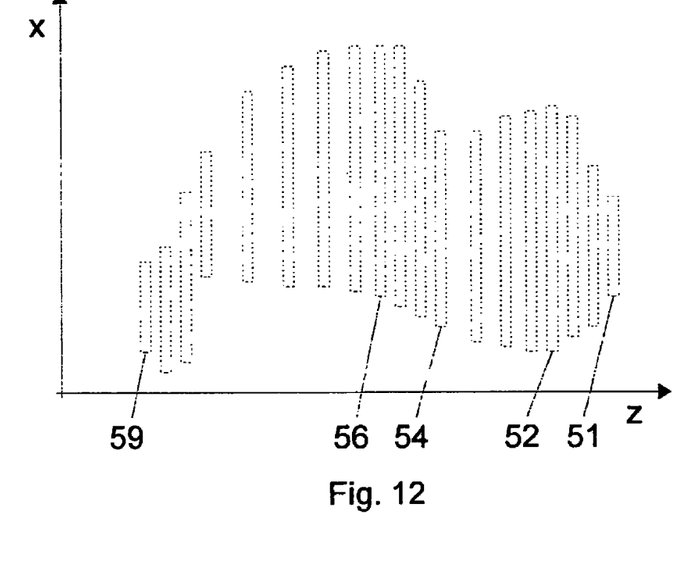
FIG. 12 shows, in diagrammatic form, a plurality of isoenergy layers.

FIGS. 11 and 12 show, in diagrammatic form, further examples of the arrangement of isoenergy layers. Differently from FIGS. 3 to 6, here the extent of the target volume in the direction perpendicular to the particle beam is shown by the extent in the x direction of the rectangle indicating the isoenergy layers.

FIG. 11 shows, in a case where the extent of the target volume in the x direction varies along the z direction, an arrangement of the isoenergy layers that is optimised in respect of the accuracy of the dose administered and in respect of minimisation of the number of target points.

The arrangement of the isoenergy layers in the view of FIG. 12 is described hereinbelow from distal to proximal. From a distal-most isoenergy layer 51 up to an isoenergy layer indicated by reference numeral 52, each isoenergy layer has target points which, in the direction perpendicular to the particle beam, are located outside the isoenergy layers at higher particle energies and therefore have no pre-dose. From the distal-most isoenergy layer 51 up to the isoenergy layer 52, the spacing between next adjacent isoenergy layers therefore remains the minimum spacing.

From isoenergy layer 52 up to an isoenergy layer 54, the cross-section of the target volume decreases. Accordingly, the minimum pre-dose within an isoenergy layer increases and the spacing between next adjacent isoenergy layers can be selected to be increasingly large.

Proximally of the isoenergy layer 54 there can be seen two isoenergy layers which each comprise target points without a pre-dose. The spacing between next adjacent isoenergy layers therefore once again has the minimum value. From an isoenergy layer 56, once again each isoenergy layer has exclusively target points which, in a projection parallel to the z direction, are located completely within the respective next distal isoenergy layer. The spacings between next adjacent isoenergy layers can therefore be selected to increase.

Immediately before the proximal-most isoenergy layer there are then once again two isoenergy layers which each comprise target points without a pre-dose.

Figure 13:
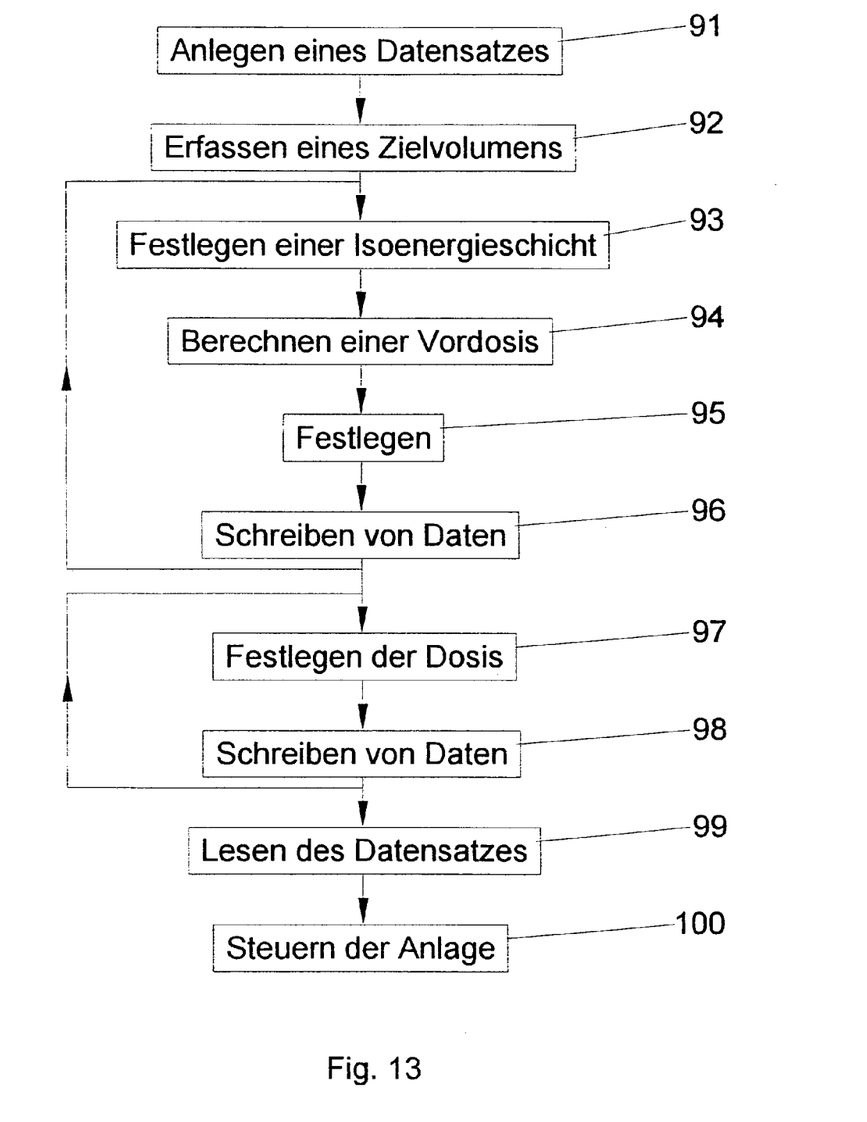
FIG. 13 shows, in diagrammatic form, a flow diagram of a method of generating a data set and of controlling a system.

FIG. 13 shows, in diagrammatic form, a flow diagram of a method of creating a data set and of controlling an irradiation system. The first eight steps 91 to 98 are performed, for example, with the aid of the apparatus 81 described above with reference to FIG. 2. The result can be an arrangement of target points as described above with reference to FIGS. 3 to 12. The last two steps 99, 100 are performed, for example, by the controller 86 described above with reference to FIG. 2.

In a first step 91, the data set is created. In a second step 92, a target volume is detected, for example by means of the tomograph 71 described above with reference to FIG. 2 and the apparatus 81 likewise described above with reference to FIG. 2.

The third step 93, the fourth step 94, the fifth step 95 and the sixth step 96 are performed for each individual isoenergy layer within the target volume. On so doing, in each case first of all in the third step 93 an isoenergy layer is specified, for example by defining the co-ordinates of the target points within the isoenergy layer. In a fourth step 94, for each individual target point of the isoenergy layer there is calculated the pre-dose produced at the target point in question on direction of the particle beam at target points at higher particle energy.

In a fifth step 95, in dependence upon the pre-doses calculated in the fourth step 94 and the desired doses associated with the target points, one or more parameters for the entire energy layer or for individual target points from the isoenergy layer are specified. Those parameters describe the spacing, measured in the direction parallel to the particle beam, of the target point or of the isoenergy layer from the next adjacent target point or from the next adjacent isoenergy layer, respectively, and/or the extent of the spatial distribution of the dose distribution to be produced by direction of the particle beam at a target point in the direction parallel to the particle beam and/or in the directions perpendicular to the particle beam. In addition, the parameters can describe the spacing between next adjacent target points within an isoenergy layer.

The parameters specified in the fifth step 95 can relate to the respective next isoenergy layer with a lower particle energy or to the spacing therefrom. Alternatively, the parameters specified in the fifth step 95 relate to the isoenergy layer the pre-doses of which were calculated in the fourth step 94. When the parameters include the layer spacing, the fifth step 95 can include a correction of the position of the isoenergy layer specified in the third step 93 or an iterative optimisation thereof.

In the specifying of the parameters in the fifth step 95 it is also possible to use the above-described information relating to movements of the body being irradiated; in regions subject to strong movement, for example, a smaller spacing between target points or between isoenergy layers or a broader dose distribution (especially in the direction of movement) is selected.

In a simplified variant, the parameters are specified in dependence upon the isoenergy layer or a number of the isoenergy layer; for example, the spacing between the isoenergy layers is a function of their number.

In a sixth step 96, the data or parameters specified in the fifth step 95 are entered in the data set created in the first step 91.

In the above-described steps of the method shown in FIG. 13, it is also possible for the doses or numbers of particles to be administered on direction of the particle beam at the individual target points to be specified and entered in the data set created in the first step 91. Alternatively, those doses or numbers of particles are entered in a separate data set. In accordance with a further alternative, those doses are specified only after complete specifying of all target points in respect of their spatial positions and the extents of the dose distributions in a seventh step 97 and, in an eighth step 98, entered in the data set generated in the first step 91 or in some other data set.

The target points defined by the data set so generated can have, especially, the features described above with reference to FIGS. 3 to 12, and also in combinations not shown in FIGS. 3 to 12.

The data set generated in the steps described above can be stored, subjected to quality control, corrected or transmitted. Finally, in a ninth step 99, it can be read or received and then, in a tenth step 100, used for controlling an irradiation system.

The steps described above can be performed in a number of separate methods and at different times. For example, steps 91 to 96 and optionally steps 97 and 98 are performed some time before the irradiation. The ninth step 99 and the tenth step 100 are performed immediately before or during the irradiation.

The described exemplary embodiments are not only suitable for use in the context of particle therapy. They are also generally suitable for use in systems for irradiating matter, especially when the beam dose administered is to vary spatially or is to be restricted to a target volume, and also when the matter is moving relative to the reference system of the system or is being moved relative to the reference system of the system.

The present invention is not limited to the embodiments described herein; reference should be had to the appended claims.

The invention claimed is:

1. A method of generating a data set defining a plurality of target points in a target volume in a body at which a particle beam is to be directed in a continuous or discontinuous process, so as to provide a spatial dose distribution in an area around the respective target points, each of the target points having a z-spacing from an adjacent target point, and a respective spacing from an adjacent target point in a direction perpendicular to the direction of the particle beam, the method comprising:
  defining the target points in the data set by the following parameters:
    z-spacing, the z-spacing being a distance, measured in a direction of the particle beam in a homogenous body equivalent to the body, between the respective target point and an adjacent target point at different depth corresponding to a higher or lower particle energy,
    respective spacing in a direction perpendicular to the direction of the particle beam, and
    the spatial dose distribution,
  wherein at least one of the parameters is varied throughout the data set in dependence upon a particle energy of the target points.

2. The method as recited in claim 1, wherein the z-spacing is a monotonic function of the particle energy.

3. The method as recited in claim 1, wherein the z-spacing each target point is greater for a lower particle energy than for a higher particle energy.

4. The method as recited in claim 1, wherein the z-spacing for a selected target point from the next adjacent target point at a higher or lower particle energy is determined by:
  calculating a pre-dose to be produced at the selected target point by directing the particle beam to a target point with a higher particle energy; and
  determining the z-spacing in dependence upon the calculated pre-dose and upon a desired dose of the selected target point.

5. The method as recited in claim 4, wherein the z-spacing for the selected target point from the next adjacent target point at a higher particle energy is determined such that a ratio between a dose to be produced at the selected target point and a desired dose at the selected target point does not exceed a threshold value.

6. The method according to claim 1, further comprising:
arranging the plurality of target points in isoenergy layers; and
determining a z-spacing of a first isoenergy layer from a second isoenergy layer having a higher or a lower particle energy by:
calculating a pre-dose of first target points in the first isoenergy layer that is to be produced by directing the particle beam to second target points in the second isoenergy layer with the higher energy; and
defining the z-spacing of the first isoenergy layer from the second isoenergy layer in dependence upon the calculated pre-dose of the first target points and a desired dose of the first target points.

7. The method according to claim 6, wherein the z-spacing of the first isoenergy layer from the second isoenergy layer is determined in dependence upon a maximum ratio or a maximum difference between the desired dose and the calculated pre-dose of the first target points in the first isoenergy layer.

8. The method according to claim 6, wherein the z-spacing of the first isoenergy layer from the second isoenergy layer with a higher or lower particle energy is determined so that a ratio between a dose that is to be produced at the first target points in the first isoenergy layer and the desired dose for the first target points in the first isoenergy layer do not exceed a predetermined threshold value for any first target points in the first isoenergy layer.

9. The method according to claim 1, further comprising entering further data to the data set, the further data defining a cross-section of the particle beam for each of the target points.

10. The method according to claim 9, wherein the cross-section of the particle beam is a monotonic function of the particle energy.

11. The method according to claim 9, wherein the cross-section of the particle beam is smaller for a lower particle energy than the cross-section of the particle beam for a higher particle energy.

12. The method according to claim 9, further comprising defining the cross-section of the particle beam at each target point by:
calculating a pre-dose to be produced at the respective target point by directing the particle beam to a target point with a higher particle energy; and
defining the cross-section in dependence upon the calculated pre-dose and a desired dose at the respective target point.

13. The method according to claim 9, further comprising the steps of:
arranging the plurality of target points in isoenergy layers; and
defining the cross-section of the particle beam at first target points in the first isoenergy layer by:
calculating a pre-dose to he produced at the first target points in the first isoenergy layer by the directing the particle beam to second target points having a higher particle energy; and
defining the cross-section of the particle beam at the first target points in the first isoenergy layer in dependence upon the calculated pre-dose and a desired dose at the first target points in the first isoenergy layer.

14. The method according to claim 1, further comprising defining a width of a Bragg peak of the particle beam for each of the plurality of target points.

15. The method according to claim 14, wherein the width of the Bragg peak is a monotonic function of the particle energy.

16. The method according to claim 14, wherein the width of the Bragg peak at a lower particle energy is smaller than the width of the Bragg peak at a higher particle energy.

17. The method according to claim 14, wherein the step of defining the width of the Bragg peak includes:
calculating a pre-dose to be produced at the selected target point by directing the particle beam to target points having a higher particle energy; and
defining the width of the Bragg peak in dependence upon the calculated pre-dose and a desired dose at the selected target point.

18. The method according to claim 1, further comprising:
arranging the plurality of target points in isoenergy layers;
defining the width of a Bragg peak at first target points in a first isoenergy layer by:
calculating a pre-dose to be produced at the first target points in the first isoenergy layer by directing the particle beam at second target points with a higher particle energy; and
defining the cross-section of the particle beam at the first target points in the first isoenergy layer in dependence upon the calculated pre-dose and a desired dose at the first target point in the first isoenergy layer.

19. The method according to claim 1, in which the z-spacing or the spatial dose distribution are defined such that the difference between a dose and a desired dose does not exceed a predetermined threshold value at any location in the target volume.

20. The method according to claim 1, further comprising entering further data to the data set, the further data defining for each target point a desired value for a dose to be produced at the target points by directing the particle beam at the target points.

21. The method according to claim 1, further comprising entering further data to the data set, the further data defining for each target point a number of particles to be administered by directing the particle beam at the target points in the target volume.

22. The method according to claim 1, further comprising detecting a movement of at least a portion of the target volume, wherein the target points in the data set are defined by at least one of the respective z-spacings and the spatial dose distributions in dependence upon the movement detected.

23. The method according to claim 22, wherein the movement is detected before irradiation.

24. The method according to claim 1, wherein the data set comprises control parameters for an irradiation system.

25. The method according to claim 24, further comprising:
reading the data set;
controlling the irradiation system.

26. A computer program product having instructions for controlling the method according to claim 1 for implementation of the computer program product on a computer.

27. A system for irradiation of a predetermined target volume in a body, the system comprising:
a particle beam generation device; and
a controller configured to:
direct a particle beam to each of a plurality of target points so as to provide a spatial dose distribution in an area around the respective target points, the target points each having a z-spacing from an adjacent target point and a respective spacing from an adjacent target point in a direction perpendicular to the direction of the particle beam; and define the target points in the data set by the following parameters:
    z-spacing, the z-spacing being a distance, measured in a direction of the particle beam in a homogenous body equivalent to the body, between the respective target point and an adjacent target point at different depth corresponding to a higher or lower particle energy,
    spacing in a direction perpendicular to the direction of the particle beam, and
    the spatial dose distribution,
wherein at least one of the parameters is varied throughout the data set in dependence upon a particle energy of the target points.

28. The controller according to claim 27, wherein the controller has an output for controlling at least one of the z spacings, a cross-section of the particle beam and a width of a Bragg peak.

* * * * *